| United States Patent [19] | [11] Patent Number: 4,922,011 |
| Takahashi et al. | [45] Date of Patent: May 1, 1990 |

[54] METHOD FOR PURIFYING ASPARTIC ACID

[75] Inventors: Satoji Takahashi, Mieken; Masao Nakamura, Kawasaki, both of Japan

[73] Assignee: Ajinomoto Company, Ltd., Tokyo, Japan

[21] Appl. No.: 167,113

[22] Filed: Mar. 11, 1988

[30] Foreign Application Priority Data

Mar. 20, 1987 [JP] Japan ................................ 067671

[51] Int. Cl.$^5$ ............................................ C07C 99/12
[52] U.S. Cl. ................................................. 562/554
[58] Field of Search ............... 560/171; 562/554, 571, 562/593; 260/701, 704, 707

[56] References Cited

U.S. PATENT DOCUMENTS 3,565,950 2/1971 Ito et al. ........................ 562/554
3,644,514 2/1972 Bornengo et al. ................ 562/554

OTHER PUBLICATIONS

Greenstein, Winitz, "Aspartic Acid and Asparagine", Chemistry of the Amino Acids 3 (*John Wiley*, New York, 1961), pp. 1856–1878.

*The Merck Index*, (1983), 10th Ed., An Encyclopedia of Chemicals, Drugs and Biologicals, p. 844.

*Primary Examiner*—Michael L. Shippen
*Attorney, Agent, or Firm*—Oblon, Spivak, McClelland, Maier & Neustadt

[57] ABSTRACT

A method for purifying aspartic acid comprising suspending aspartic acid crystals containing chloride ion impurities in an aqueous solution at a temperature of 50° C. or higher, followed by separating the purified aspartic acid crystals, is disclosed.

6 Claims, No Drawings

METHOD FOR PURIFYING ASPARTIC ACID

BACKGROUND OF THE INVENTION

1. Field of the Invention

The present invention relates to a method for purifying aspartic acid, and more specifically, it relates to a method for obtaining high purity aspartic acid from which $Cl^-$ has been reduced or removed.

2. Description of the Related Art

Aspartic acid has heretofore been produced by a fermentation process, an enzymatic process and a chemical synthetic process, and its purification is carried out by using various purification techniques in combination.

In any production process, since the obtained crude aspartic acid crystals contain impurities such as other amino acids, colored substances, inorganic salts, etc., their purification requires a lot of labor and cost. Especially in the case where high purity aspartic acid crystals are to be obtained, it is usual practice to dissolve the entire quantity of the crude crystals once and to carry out such techniques as ion exchange resin treatment, decoloring treatment, crystallization, etc.

The present invention aims to solve the problem that the crude aspartic acid crystals obtained by the above-described prior art processes contain impurities, and to obtain high purity aspartic acid.

SUMMARY OF THE INVENTION

The present inventors have intensively sought a method for easily removing impurities contained in crude aspartic acid crystals and, as a result, have surprisingly discovered that the impurities may be removed by suspending the crude aspartic acid crystals in an aqueous solution and stirring at a high temperature. Although the impurities cannot be removed when the crystals are suspended at a low temperature, such as 10°–40° C., the impurities are suddenly reduced at a temperature of 50° C. or higher. This is a characteristic property of aspartic acid crystals.

DESCRIPTION OF THE PREFERRED EMBODIMENTS

According to the present invention, other amino acids, colored substances and inorganic salts, especially $Cl^-$, contained in the crude crystals in very slight amounts may be greatly reduced. Generally, the amount of chloride ion contained in the crude crystals before purification will range from about 200 to about 5,000 ppm, based on the aspartic acid molecules. Preferably, the starting concentration of the chloride ion will be from about 300 to about 5,000 ppm. After purification, the aspartic acid crystals will generally have a concentration of not more than 100, preferably not more than 50 ppm chloride. The lower limit could be as low as 0–5 ppm.

Crude aspartic acid crystals crystallized from a solution containing amino acids other than aspartic acid and sodium chloride tend to contain other amino acids and sodium chloride, and upon purification of such crude aspartic acid crystals, the present invention is extremely effective. Some examples of other impurities which can be reduced by the present process are, for example, alanine, proline, glutamic acid, $SO_4^{2-}$, etc. The amounts of these materials before and after purification can be the same as the amounts given for chloride above.

The temperature of the suspension is satisfactorily 50° C. or higher, and an easily operable temperature range is suitably 55°–90° C. The suspension time depends on the temperature, but 5 minutes or longer will usually suffice and, in general, a range of 10–120 minutes is satisfactory. The concentration of the crude aspartic acid crystals may be the concentration suspended and is not particularly restricted, and in general the operation is conducted at 5–40 g/dl.

The operational procedures of the present invention may comprise either adding the crude aspartic acid crystals first, then adding water and raising the temperature, or adding the crude aspartic acid crystals to heated water. The purifying effect may be enhanced by stirring so that the crystals flow appropriately.

After practicing the present invention, the crystals may be separated directly, but in order to increase the yield, it is generally preferred to separate after cooling to 5°–25° C.

According to the present invention, the effect of purification of other amino acids, colored substances and inorganic salts such as sodium chloride from the crude aspartic acid crystals is extremely great, and high purity aspartic acid crystals may be easily obtained without carrying out other purification procedures.

Therefore, since the present method does not require conventional purification such as ion exchange resin treatment, crystallization etc. and the operation is quite easy without reducing the yield, this is an extremely advantageous method from an industrial point of view.

The invention now being generally described, the same will be better understood by reference to certain specific examples which are included herein for purposes of illustration only and are not intended to be limiting of the invention or any embodiment thereof, unless specified.

EXAMPLE 1

50 g of crude L-aspartic acid crystals containing 360 ppm of $Cl^-$ and 250 ml of water were mixed. Three such mixtures were heated to temperatures of 60° C., 70° C. and 80° C. respectively, and stirred for 40 minutes, respectively. Thereafter, they were cooled to room temperature (25° C.), and stirred for 2 hours. The crystals were filtered through filter paper and the crystals were washed with 20 ml of cold water (5° C.), respectively. The $Cl^-$ content in the L-aspartic acid crystals obtained after drying was measured by silver nitrate titration analysis. The $Cl^-$ content of the L-aspartic acid crystals as a result of treatment at the respective temperatures is shown in Table 1.

TABLE 1

|  | Before Treatment | After Treatment at 60° C. | After Treatment at 70° C. | After Treatment at 80° C. |
|---|---|---|---|---|
| $Cl^-$ Content (ppm) | 360 | 80 | Not Detected (not more than 5 ppm) | Not Detected (not more than 5 ppm) |

COMPARATIVE EXAMPLE

Similar procedures were carried out except that the temperature in Example 1 was replaced by 40° C. As a result, the $Cl^-$ content in the L-aspartic acid crystals was 250 ppm.

EXAMPLE 2

50 g of L-aspartic acid crystals containing 1000 ppm of $Cl^-$ and 0.1% of L-glutamic acid and which were colored yellowish brown was added to 250 ml of water heated to 50° C., then further heated to 80° C. with stirring, and stirred for 30 minutes. Thereafter, the solution was cooled to 25° C. and centrifugally separated 2 hours later. The obtained L-aspartic acid crystals were colorless, and when measured for $Cl^-$ by silver nitrate titration analysis, $Cl^-$ was not detected. Further, when measured by an amino acid analyzer, L-glutamic acid was not detected either. The yield of L-aspartic acid was 43 g.

APPLICATION EXAMPLE

Ten ml of an aqueous solution (adjusted to pH 5.4) containing 5 g of the L-aspartic acid crystals obtained in Example 1 and 10 g of L-phenylalanine methyl ester obtained by the procedures described below was aseptically added to a culture liquor of *Brevibacterium linens* ATCC 8377 which had been cultured by using the medium described below at 30° C. for 12 hours, then the pH of the culture liquor was aseptically adjusted to 5.4, and culture was further carried out for 10 hours. During culture, the pH was aseptically controlled to 5.4 at intervals of 2 hours.

Measurement of the product in this culture liquor by an amino acid analyzer showed that 315 mg/dl of APM had been produced.

Preparation of L-Phenylalanine Methyl Ester (PM)

279.0 g of wet crystals of L-Phe ½ sulfate hemihydrate (20% of adsorbed water based on the total weight, 1.00 mole as L-Phe) was suspended in 250 ml of MeOH and, after adding 60 ml of 98% sulfuric acid, reacted at 85° C. for 4 hours. The reaction was carried out while distilling off the water and MeOH and replenishing the MeOH.

The PM in the obtained reaction mixture was quantitatively analyzed by high performance liquid chromatography, to obtain a yield of 99%.

MEDIUM

Fifty ml of a medium (pH 7.0) containing 2.0 g/dl of glucose, 0.5 g/dl of $(NH_4)_2SO_4$, 0.1 g/dl of $KH_2PO_4$, 0.05 g/dl of $MgSO_4.7H_2O$, 1 mg/dl of $FeSO_4.7H_2O$, 1 mg/dl of $MnSO_4.4H_2O$, 1.0 g/dl of yeast extract, 0.5 g/dl of malt extract, and 4.0 g/dl of calcium carbonate (separately sterilized) was added to a flask having a capacity of 500 ml, and sterilized at 120° C. for 15 minutes.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A method for purifying aspartic acid which comprises suspending impure aspartic acid crystals containing as an impurity at least chloride ion, in an aqueous solution at a temperature of 50° C. or higher to form a suspension, maintaining said suspension for at least 5 minutes and separating purified aspartic acid crystals from said aqueous solution.

2. A method according to claim 1, wherein said temperature ranges from 50° to 90°.

3. A method according to claim 1, wherein said suspending is carried for from 10 minutes to 120 minutes.

4. A method according to claim 1, wherein the concentration of aspartic acid in said aqueous solution is 5 g/dl to 40 g/dl.

5. A method according to claim 1, wherein after said purifying, the aspartic acid is separated by cooling said solution to 5° C. to 25° C.

6. A method according to claim 1, wherein the amount of chloride ion in said impure aspartic acid crystals ranges from 200 to 5000 ppm, and the amount of chloride in said purified aspartic acid crystals is not more than 100 ppm.

* * * * *